(12) United States Patent
Offermann

(10) Patent No.: US 10,537,914 B2
(45) Date of Patent: *Jan. 21, 2020

(54) METERING DEVICE FOR THE MANUALLY-CONTROLLED METERING OF A LIGHT-CURING MATERIAL, KIT, AND METHOD

(71) Applicant: Thomas Offermann, Eppan (IT)

(72) Inventor: Thomas Offermann, Eppan (IT)

(73) Assignee: LASER BONDING TECH INC., Aurora (CA)

( * ) Notice: Subject to any disclaimer, the term of this patent is extended or adjusted under 35 U.S.C. 154(b) by 118 days.

This patent is subject to a terminal disclaimer.

(21) Appl. No.: 14/355,624

(22) PCT Filed: Oct. 31, 2012

(86) PCT No.: PCT/EP2012/004551
§ 371 (c)(1),
(2) Date: May 1, 2014

(87) PCT Pub. No.: WO2013/064248
PCT Pub. Date: May 10, 2013

(65) Prior Publication Data
US 2014/0284352 A1    Sep. 25, 2014

(30) Foreign Application Priority Data
Nov. 2, 2011   (DE) .......... 10 2011 117 405

(51) Int. Cl.
*B65D 83/00* (2006.01)
*B05C 9/10* (2006.01)
*A61C 13/15* (2006.01)
*G03F 7/16* (2006.01)
*B05C 17/005* (2006.01)

(52) U.S. Cl.
CPC .............. *B05C 9/10* (2013.01); *A61C 19/004* (2013.01); *B05C 17/00583* (2013.01); *B65D 83/0055* (2013.01); *G03F 7/16* (2013.01)

(58) Field of Classification Search
CPC ....... G03F 7/16; B65D 83/0055; A61C 5/062; A61C 19/004
USPC .............................. 222/113, 92, 93, 105, 106
See application file for complete search history.

(56) References Cited

U.S. PATENT DOCUMENTS 1,382,134 A * 6/1921 Stafford .................... 222/105
1,961,489 A * 6/1934 Hein ........................... 604/214
(Continued)

FOREIGN PATENT DOCUMENTS

AT          160436 B      5/1941
AT          160436 B1     5/1941
(Continued)

*Primary Examiner* — J C Jacyna
(74) *Attorney, Agent, or Firm* — Abel Schillinger, LLP

(57) ABSTRACT

The invention relates to a metering device (100) for metering, in a manually-controlled manner, a light-curing material present in said metering device (100), the device comprising at least one reservoir (1) which can be deformed at least in some sections thereof and in which said light-curing material is contained, as well as a metering arrangement (3) for applying the light-curing material. The invention also relates to a kit and a method.

14 Claims, 2 Drawing Sheets

(56) References Cited

U.S. PATENT DOCUMENTS

| | | | |
|---|---|---|---|
| 3,240,405 A * | 3/1966 | Abbott | B65D 47/0838 |
| | | | 222/543 |
| 4,437,582 A | 3/1984 | Doerner | |
| 6,578,772 B2 | 6/2003 | Fujimoto et al. | |
| 8,403,008 B2 | 3/2013 | Bouix et al. | |
| 8,602,774 B2 | 12/2013 | Wasylucha | |
| 8,662,350 B2 | 3/2014 | Nakatsuka et al. | |
| 2001/0025890 A1 | 10/2001 | Fujimoto et al. | |
| 2005/0026103 A1 | 2/2005 | Wasylucha | |
| 2006/0037972 A1 * | 2/2006 | Leiner | A61C 5/062 |
| | | | 222/212 |
| 2008/0003049 A1 * | 1/2008 | Peuker | 401/183 |
| 2010/0075276 A1 | 3/2010 | Nakatsuka et al. | |
| 2010/0175348 A1 * | 7/2010 | Fundingsland et al. | 53/111 R |
| 2011/0284123 A1 | 11/2011 | Bouix et al. | |
| 2012/0241469 A1 | 9/2012 | Takeshi | |
| 2014/0099603 A1 | 4/2014 | Wasylucha | |

FOREIGN PATENT DOCUMENTS

| | | | |
|---|---|---|---|
| DE | 3137760 A1 | | 7/1983 |
| DE | 29514116 U1 | | 11/1995 |
| DE | 102010060422 A1 | † | 1/2012 |
| DE | 102011054959 A1 | † | 5/2013 |
| WO | 2005039995 A1 | | 5/2005 |
| WO | 2011058792 A1 | | 5/2011 |

\* cited by examiner
† cited by third party

METERING DEVICE FOR THE MANUALLY-CONTROLLED METERING OF A LIGHT-CURING MATERIAL, KIT, AND METHOD

BACKGROUND OF THE INVENTION

1. Field of the Invention

The present invention relates to a metering device for metering, in a manually controlled manner, a light-curing material. The invention relates further to a kit comprising the metering device as well as to a method employing the metering device.

2. Discussion of Background Information

By means of a metering device, materials of different viscosities are metered or dosed for various purposes. The materials may be fluid, semi-fluid, in a form of a paste and so on. The metering device, depending on application and purpose of use, may be operated in fully-automated, partly-automated or manual manner.

An object of the present invention is to propose a further metering device. Further, a kit having at least one such metering device and a housing is to be proposed. In addition, a method for applying a metering medium and/or for curing light-curing material is to be provided.

SUMMARY OF THE INVENTION

According to the invention a metering device is thus proposed for manually controlled metering—or for metering by means of pressure using the finger—a light-curing material contained in the metering device. The metering device comprises at least one reservoir which can be deformed in sections thereof, in particular in a manual manner. This reservoir contains the light-curing material. The metering device comprises further a metering arrangement which is flown through by the light-curing-material upon its application.

The kit according to the invention comprises at least a metering device according to the invention and at least one housing. The housing is prepared, for example by providing a suitable device, for receiving the metering device on the housing in a detachable manner.

The method according to the invention serves for applying and/or curing of light-curing material by using the metering device.

In all of the following embodiments, the use of the expression "may" or "may have", etc. is to be understood as a synonym to "is preferably" or "preferably has", etc. and it is to explain an exemplary embodiment according to the invention.

Developments of the present invention are each the subject-matter of dependent claims and embodiments.

Embodiments according to the present invention may comprise one or more of the following features in any arbitrary combination.

In certain embodiments according to the invention, the metering arrangement comprises a metering channel, through which the light-curing material is extracted or applied. Thereby, the metering arrangement, in particular or preferably entirely or essentially, is made of a first material or comprises a first material, while the metering channel, in particular or preferably entirely or essentially, is made of a second material, or comprises such material. The second material differs from the first material.

The reservoir is, in certain embodiments according to the invention, a container or cartridge.

In some embodiments according to the invention, the metering channel is made of a metallic material or an alloy, or comprises either of such material.

In certain embodiments according to the invention, the metering arrangement is connected to the metering device in a detachable manner.

In particular embodiments according to the invention, the metering arrangement is connected to the metering device by means of a thread, wherein the metering arrangement and the metering device carry a portion of the thread or a portion of the joint thread each.

In some embodiments according to the invention, the metering device comprises a sealing arrangement, such as a sealing ring for example in the form of an O-ring. By means of the sealing arrangement, it is advantageously possible to achieve a seal between the metering device or the reservoir on the one hand and the sealing arrangement on the other hand, relative to an exterior or the environment or an outside.

In certain embodiments according to the invention, the metering arrangement is made of, with respect to the metering device, a harder material or at least comprises a harder material. This design may advantageously help or guarantee in some embodiments that the seal is sustained between the metering arrangement and the metering device also upon elastic deformation of the metering arrangement, for example, by applying pressure thereto.

In some embodiments according to the invention, the housing of the kit is made of the same material (e.g., polyethylene (PE)) as the reservoir itself, or it comprises such material.

In certain embodiments according to the invention, the reservoir is filled or provided to be filled with a substance other than a light-curing material, for instance with oil, food, color or a color mixture, paint or a paint mixture or pasty materials of any kind. In these embodiments the term "light-curing material" as used anywhere herein, is to be extended on the above-mentioned substances. In these embodiments, the term "light-curing material", as it is at any point used herein shall be understood as synonymous with the aforementioned substances.

In some embodiments according to the invention, the reservoir is transparent or at least has a transparent section. This advantageously allows a visual control of the filling level of the reservoir.

In certain embodiments according to the invention, the light emitting device is solidly integrated in the housing. In other embodiments according to the invention, the kit comprises at least one optical fiber (glass fiber, etc. . . . ) which guides the light from the light emitting device (which is arranged in a rear section of the kit) to the metering arrangement or near an outlet opening thereof (arranged in the front of the kit).

In specific embodiments according to the invention, the operation of the light-emitting device is initiated by means of a push button.

In some embodiments according to the invention, the housing of the kit is manufactured of a metal (aluminum, stainless steel, titanium, etc.) or comprises such a material.

In certain embodiments according to the invention, an internal gas cartridge and/or other arrangement is provided to build up pressure in order to increase the pressure within the reservoir. This may be advantageous for a more comprehensive emptying of the reservoir. Furthermore, this may allow also an overhead working with the kit according to the invention.

In some embodiments according to the invention, the reservoir comprises in at least a section thereof and/or in its lateral surface or in a main area thereof, respectively, a wall thickness in a range of 0.75 to 1.25 mm, preferably from 0.9 to 1.1 mm, again preferably in a range from 0.95 to 1.05 mm. These ranges have been found to be particularly suitable with regard to the desired ductility and the required stability and capacity.

In certain embodiments according to the invention, the metering device comprises light-curing material which cures by means of radiation in a range of 380 to 500 nanometers (nm), in particular in the range of 450 to 480 nm, particularly at 470 nm, and in particular in a range of 390 to 410 nm, particularly at 405 nm.

In some embodiments according to the invention, the reservoir is made of a light impermeable material. The light impermeable material is preferably, at least, or particularly impermeable to a radiation range of 380 to 500 nanometers (nm), in particular in the range of 450 to 480 nm, particularly at 470 nm, and in particular in a range of 390 to 410 nm, particularly at 405 nm.

In certain embodiments according to the invention, the metering arrangement and/or the metering channel comprise a detachable closure against an exterior (i.e. the environment). In some embodiments according to the invention, the closure is a cap.

In some embodiments according to the invention, the closure is impermeable to light, preferably for a radiation range of 380 to 500 nanometers (nm), in particular in the range of 450 to 480 nm, particularly at 470 nm, and in particular in a range of 390 to 410 nm, particularly at 405 nm.

In certain embodiments according to the invention, the metering channel and the light emitting device are embodied or provided on two opposite end sections of the kit or of the metering device. By simply turning the kit or the metering device it is possible without changing hands, with only one hand, to extract the light-curing material as well as to cure them by means of the light emitting device.

In some embodiments according to the invention, the light emitting device for the curing of the light-curing material is a LED lamp and/or a flash means or comprises the like.

In certain embodiments according to the invention, the housing is embodied to receive the light emitting arrangement in a detachable manner. This can be done for example by inserting, clicking, seizing, clamping or the like. The housing may be prepared accordingly.

In specific embodiments according to the invention, the housing and the metering device, in particular the metering arrangement of the metering device comprise a bayonet closure or corresponding parts of a bayonet closure for receiving the metering device in or on the housing in a detachable manner.

In certain embodiments according to the invention, the housing comprises at least one opening for the manually controlled metering of the light-curing material where, by means of the user's finger by means of the one or more openings through the housing or the wall thereof, the reservoir may be contacted from outside of the housing and suitable pressure may be applied thereto.

For this purpose, the housing comprises, in specific embodiments according to the invention, two, preferably opposite, openings. In other embodiments according to this invention, there are more than two openings.

In some embodiments according to the invention, the at least one opening is located in a lateral surface or shell surface of the housing. In certain embodiments according to the invention, the at least one opening is not located in an end face thereof.

What is herein being set forth to one opening, applies to two, three or more or all of the available openings in certain embodiments according to the invention.

In specific embodiments according to the present invention, at least one of the openings comprises a longitudinal direction and a transverse direction perpendicular thereto, wherein the opening extends longitudinally through a further distance in the wall of the housing than in the transverse direction, or vice versa.

In certain embodiments according to the invention, the opening in the circumferential direction comprises at least two sections of different widths. Such an opening is thus at a point or section wider (in the circumferential direction of the housing) than in another point or section.

In some embodiments according to the invention, the metering device or the housing, comprise a device for receiving the light-emitting device in a detachable manner. This device is embodied in particular embodiments according to the invention as a snap-on device. In other embodiments according to the invention, this device is embodied as a plug device and the like.

In some embodiments according to the invention, the light-emitting device comprises a switch, by means of which it can be placed in a continuous emitting operation.

In certain embodiments according to the invention, the light-emitting device comprises an arrangement, by means of which it can be placed in an emitting operation by a pressure thereon, which lasts only for the time period in which the pressure thereon exists. This can be effected by means of a pressure switch with a return means.

In some embodiments, the method according to the invention encompasses turning or rotating of the metering device after application of light-curing material through the metering arrangement about a transverse axis of the metering device for the curing of the applied material by means of the light-emitting device which is arranged on the metering arrangement.

Any embodiments according to the invention may comprise or offer any one or more of the following advantages.

Thus, there is an advantage in the interchangeability of used or emptied-through-use metering devices whose reservoir does not comprise enough light-curing material anymore. The kit, the housing and all other components may be preserved and may continue to be used. Only the reservoir or the metering device are to be replaced. This advantageously reduces the material costs, disposal costs, the need for storage space and the like. Here, even the metering arrangement may continue to be used due to the separability or detachability of reservoir and metering arrangement in some embodiments according to the invention.

The herein proposed bayonet closure for some embodiments according to the invention, has proved its particular suitability to grant a quick, easy and reliable interchangeability.

In a number of the embodiments according to the invention, different components are made of different materials or comprise such material. Hereby a further advantageous contribution to the tightness of the metering device against an exterior may be achieved.

A tightness between the individual components with the proposed sealing device herein is obtained advantageously and according to the invention.

The provision of different materials may also advantageously allow, the different components of the kit independent from each other and in terms of their respective function to be produced in the most cost-effective manner, respectively.

BRIEF DESCRIPTION OF THE DRAWINGS

The present invention is exemplarily explained below with reference to the accompanying drawings, in which identical reference numerals denote the same or similar components.

In the drawings.

DETAILED DESCRIPTION OF THE INVENTION

Figure 1:
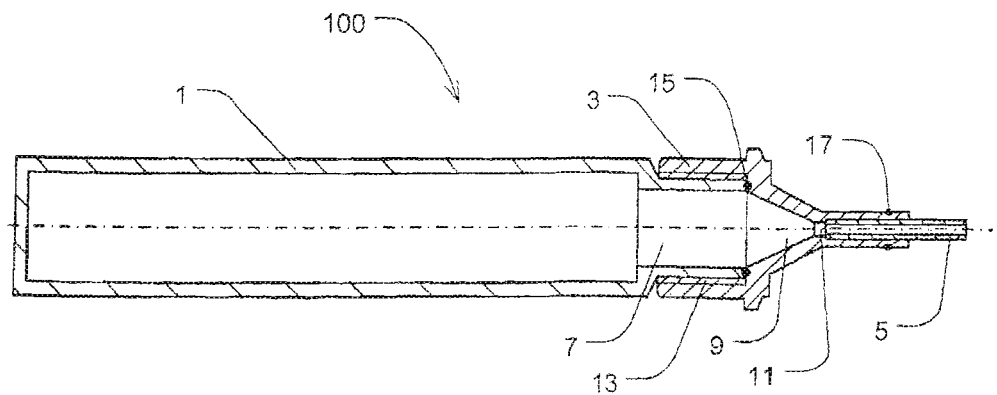
FIG. 1 shows a metering device according to the invention in a longitudinal section.

FIG. 1 shows a metering device 100 according to the invention in a sectional view in the direction of the dash-dotted longitudinal axis having a reservoir 1, a metering arrangement 3, and a metering channel 5.

The reservoir 1 comprises light-curing material (not shown here). By applying pressure onto the reservoir 1, for example by manual pressure with the finger from the outside of the deformable reservoir 1, the light-curing material is advanced or pushed through the narrowing 7 of the reservoir 1 into the metering arrangement 3. In the metering arrangement 3, the material is further advanced through a cone-shaped section, in short, cone 9, into the outlet opening 11 of the metering arrangement 3.

The metering channel 5 is inserted or advanced in the outlet opening 11 of the metering arrangement 3 until reaching a stop. The metering channel 5 may be fixed in a suitable manner. The fixation may be, for example, in form of press fitting, latching and/or bonding.

The metering channel 5 may be made of metal or an alloy. It comprises, by way of example, the following dimensions: inner diameter 0.8 mm, outer diameter 1.2 mm, length, for example, 12 mm.

The reservoir 1 is in this exemplary embodiment made of a first material, for example a soft polyethylene (for example LDPE—low density polyethylene) or comprises such material. The metering device is formed of a third material, for example, a harder polymer, with respect however to the first material a harder material, or comprises such material.

Both the first and third materials are selected (or processed, for example by a black or other types of coating or coloring) such that they are impermeable to light, preferably, at least or in particular in a light-wavelength range of 380 to 500 nanometers (nm), in order to prevent the light-curing material of the reservoir 1 and the metering arrangement 3 from an inadvertent curing by exposure to light.

The connection between the reservoir 1 and the metering arrangement 3 is exemplary embodied as a thread 13, for example by a thread M10x1. Alternatively, the connection may also be effected, for example by means of gluing, clipping, etc.

For further sealing, and possibly also in order to prevent deformation of the wall of the narrowing 7 due to the soft first material of the reservoir 1 when applying pressure onto the reservoir 1, a sealing ring 15 (for example O-ring made of polymer) in the embodiment shown here is inserted in the metering arrangement 3 for sealing the reservoir 1 about the thread 13. Through the—in particular complete—screwing of the metering arrangement 3 on the thread 13 of the reservoir 1, the connection between these two components is sealed vis-à-vis an exterior or outside by means of the sealing ring Another, optionally provided, sealing ring 17 seals between the metering arrangement 3 and a closure 19 against the exterior or outside (see FIG. 2). In addition, this further sealing ring 17 may be embodied to fix the closure 19 pushed on to the metering arrangement 3 on the metering arrangement 3.

Figure 2:
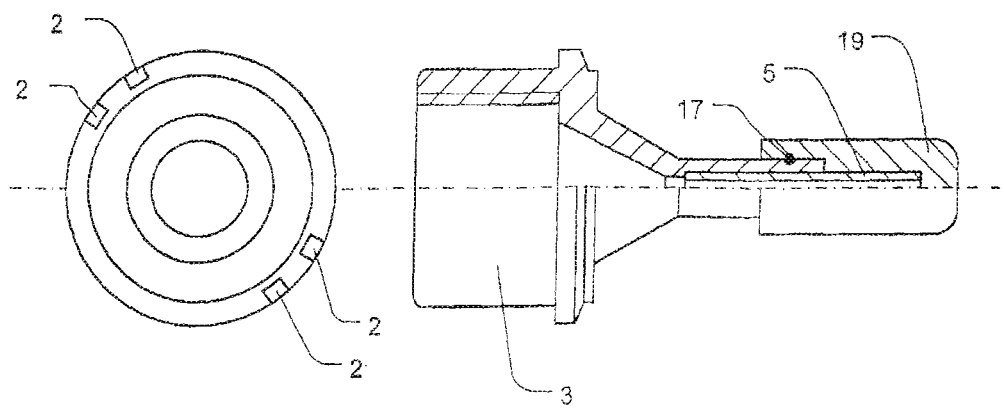
FIG. 2 shows a metering arrangement according to the invention and a closure in half-section view in the direction of the longitudinal axis and in the front view projection.

FIG. 2 shows the metering arrangement 3 according to the invention, having the metering channel 5 and the closure 19 in half sectional view in the direction of the longitudinal axis or in a level, in which the longitudinal axis lies (right illustration in FIG. 2) and in projection as front view (left illustration in FIG. 2, having closure 19).

The material of the closure is optional or preferably also impermeable to light, in particular in a light-wavelength range of 380 to 500 nanometers (nm), in order to protect the light-curing material in the metering channel 5, in particular at the outlet of the metering channel 5. against inadvertent curing by exposure to light.

The further sealing ring 17 seals as stated above the metering arrangement 3 against the closure 19 and/or fixes the inserted closure 19 on the metering arrangement 3.

In the front view (illustration on the left in FIG. 2) four notches 2 are presented on the outer ring of the metering arrangement 3. These notches 2 are parts of a bayonet closure for optional potential fixation of the reservoir 1 to the metering arrangement 3 in a housing 23 (see FIG. 3).

Figure 3A:
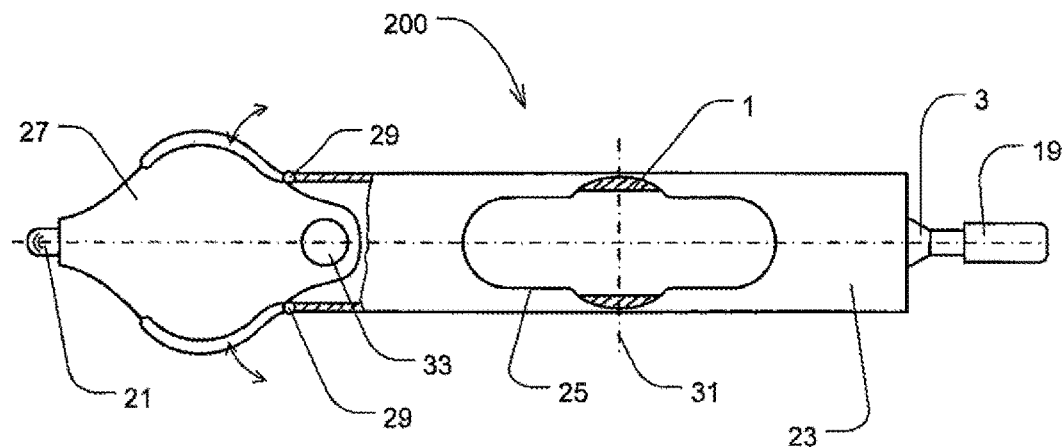
FIG. 3a, b show a kit according to the invention with the metering device, a closure for a metering channel, an LED lamp and a housing.
Figure 3B:
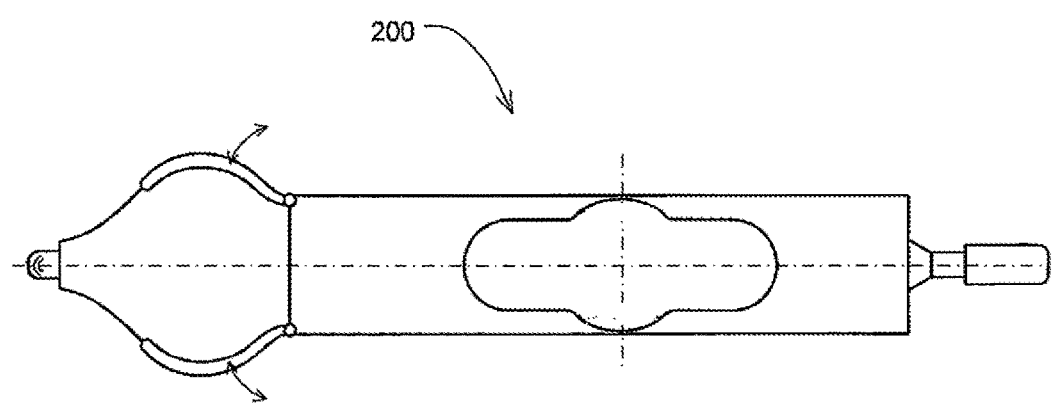

FIGS. 3a, 3b show a kit 200 according to the invention having the metering device 3, the closure 19 for the metering channel 5, an LED lamp 21 as a light emitting device and the housing 23.

In this representation, the reservoir 1 for the light-curing material is shown only partially within the housing 23.

For applying pressure to the reservoir 1 in order to advance or rather press the light-curing material out of the reservoir 1 into the metering arrangement 3 and for the discharging from the metering channel 5 (not shown in FIGS. 3a, 3b) with an open or detachable closure 19, an opening 25 is introduced in the housing 23. On the opposite rear side (not shown in FIGS. 3a, 3b) of the housing 23, at least one further, (e.g. second) opening preferably identical or similar to the opening 25, may be provided. Through this/these opening(s), a manual pressure, preferably applied by one finger each, is exerted on the reservoir 1 for applying the light-curing material.

As shown in FIGS. 3a and 3b, the opening 25 comprises an extension in the longitudinal direction thereof which extends in the longitudinal direction of the metering device 100, and a perpendicular extension thereto in transverse direction which extends perpendicularly thereto or in circumferential direction of the metering device 100 along the transverse axis or along the circumference of the metering device 100. Thereby, the opening 25 extends further in the longitudinal direction than in the transverse direction. The housing 23 or its wall is thus variably wide opened or broken through due to the relative to the longitudinal direction and the transverse or circumferential direction differently wide extensions. This allows an ergonomic reach-through to the reservoir for various sizes of the fingers of the user maintaining at the same time a sufficiently stable design of the housing 23.

After the application of the light-curing material, it may then be cured by light, in this embodiment by LED light in a wavelength range between 390 and 405 nanometers (nm). This LED light is provided by the LED lamp 21 which is received in a detachable or a non-detachable manner in an LED lamp socket 27.

The LED lamp socket 27 comprises in addition to the LED lamp a battery, a housing, a pressure switch for manually activating the LED lamp, and other mechanical and electronic elements. An activatable component for turning on a continuous operation of the LED lamp in the LED lamp socket 27 may also be obtained in the lamp socket 27.

The LED lamp socket 27 having the LED lamp 21 is a separate or singular/individual component which can be inserted into the housing 23. This has the advantage that all components required for the operation of the use of the light-curing material are available together in a compact kit 200 and may, by way of example, be transported easily.

LED lamp socket 27 is connected in a detachable manner, e.g. by plugging, to the housing 23 by means of a snap means having two spring elements 29 which may be bent apart or opened in the direction indicated by the arrows. The LED lamp socket 27 may be removed, for example by simply pulling it, out of this snap means. It is also possible to keep the LED lamp socket 27 inserted into the snap means and to activate the light-curing material by rotating the entire housing 23 (for example, about or around the transverse axis 31) and then to cure the material by means of the turned-on LED lamp 21.

By means of the opening 33 of the LED lamp socket, the LED lamp socket may be, for example, fixed or hung to facilitate the curing process if necessary.

LIST OF REFERENCE NUMERALS

| Reference Numeral | Description |
| --- | --- |
| 100 | metering device |
| 200 | kit |
| 1 | reservoir |
| 3 | metering arrangement |
| 5 | metering channel |
| 7 | narrowing of the reservoir |
| 9 | cone of the metering arrangement |
| 11 | outlet opening of the metering arrangement |
| 13 | thread |
| 15 | sealing ring between metering arrangement and reservoir |
| 17 | sealing ring between metering arrangement and closure |
| 19 | closure |
| 21 | LED lamp |
| 23 | housing |

-continued

| Reference Numeral | Description |
| --- | --- |
| 25 | opening of the housing |
| 27 | LED lamp socket |
| 29 | spring element |
| 31 | transverse axis |
| 33 | opening of the LED lamp socket |

What is claimed is:

1. A kit, wherein the kit comprises at least one metering device for metering a light-curing material contained in said metering device and at least one housing for receiving the metering device in a releasable manner, and wherein the device comprises at least one reservoir which is present in the form of a single piece comprising an opening and in which the light-curing material is present and a wall of which can be deformed at least in a section thereof; and a metering arrangement for applying the light-curing material, which metering arrangement is configured to be capable of being connected to the opening of the reservoir.

2. The kit of claim 1, wherein the kit further comprises at least one light-emitting device for curing the light-curing material.

3. The kit of claim 2, wherein the light-emitting device comprises an LED lamp.

4. The kit of claim 1, wherein a metering channel of the metering device and the light-emitting device are embodied or provided on opposite ends of the housing.

5. The kit of claim 1, wherein the housing and the metering device comprise a bayonet closure for receiving the metering device in a detachable manner.

6. The kit of claim 1, wherein the housing comprises at least one opening for metering the light-curing material in a manually-controlled manner.

7. The kit of claim 2, wherein the housing comprises a device for receiving, in a detachable manner, the light-emitting device.

8. The kit of claim 1, wherein the housing is made of or comprises the same material as the reservoir.

9. The kit of claim 7, wherein the light emitting device comprises an LED lamp and the device for receiving the light emitting device comprises a socket that is configured to be connected in a detachable manner to the housing.

10. The kit of claim 9, wherein the socket comprises a pressure switch for manually activating the LED lamp.

11. The kit of claim 1, wherein the reservoir comprises light curing material which cures in a range of from 380 nm to 500 nm.

12. The kit of claim 1, wherein the reservoir is made of a light impermeable material.

13. The kit of claim 1, wherein the reservoir is light impermeable with the exception of a transparent section for allowing visual control of a filling level of the reservoir.

14. The kit of claim 1, wherein the reservoir is present in the form of a cartridge.

* * * * *